United States Patent
Patangay et al.

(10) Patent No.: US 8,229,557 B2
(45) Date of Patent: Jul. 24, 2012

(54) ESTIMATING ACUTE RESPONSE TO CARDIAC RESYNCHRONIZATION THERAPY

(75) Inventors: Abhilash Patangay, Little Canada, MN (US); Krzysztof Siejko, Maple Grove, MN (US); Mohan Krishnan, Shoreview, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 564 days.

(21) Appl. No.: 11/729,453

(22) Filed: Mar. 29, 2007

(65) Prior Publication Data

US 2008/0243202 A1  Oct. 2, 2008

(51) Int. Cl.
*A61N 1/365* (2006.01)

(52) U.S. Cl. .......... 607/9; 607/17; 607/27; 600/509

(58) Field of Classification Search .......... 607/4, 25, 607/27, 9, 17; 600/509
See application file for complete search history.

(56) References Cited

U.S. PATENT DOCUMENTS

| | | | |
|---|---|---|---|
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,766,189 B2 | 7/2004 | Yu et al. | |
| 6,871,088 B2 * | 3/2005 | Chinchoy | 600/510 |
| 6,963,777 B2 | 11/2005 | Lincoln | |
| 7,142,922 B2 | 11/2006 | Spinelli et al. | |
| 2002/0161307 A1 * | 10/2002 | Yu et al. | 600/509 |
| 2004/0106960 A1 | 6/2004 | Siejko et al. | |
| 2004/0122479 A1 * | 6/2004 | Spinelli et al. | 607/27 |
| 2006/0020294 A1 | 1/2006 | Brockway et al. | |
| 2007/0055317 A1 | 3/2007 | Stahmann et al. | |

FOREIGN PATENT DOCUMENTS

| | | |
|---|---|---|
| WO | WO 2006049538 | 5/2006 |
| WO | WO 2006086435 | 8/2006 |

OTHER PUBLICATIONS

Office Action with translation from JP Application No. 2009-548346 dated Nov. 22, 2011, 4 pages.

* cited by examiner

*Primary Examiner* — Carl H Layno
*Assistant Examiner* — Pamela M Bays
(74) *Attorney, Agent, or Firm* — Hollingsworth Davis, LLC

(57) ABSTRACT

Systolic timing intervals are measured in response to delivering pacing energy to a pacing site of a patient's heart. An estimate of a patient's acute response to cardiac resynchronization therapy (CRT) for the pacing site is determined using the measured systolic timing intervals. The estimate is compared to a threshold. The threshold preferably distinguishes between acute responsiveness and non-responsiveness to CRT for a patient population. An indication of acute responsiveness to CRT for the pacing site may be produced in response to the comparison.

18 Claims, 8 Drawing Sheets

ESTIMATING ACUTE RESPONSE TO CARDIAC RESYNCHRONIZATION THERAPY

FIELD OF THE INVENTION

The present invention relates generally to cardiac pacing therapy, and more specifically, to estimating a patient's acute response to cardiac resynchronization therapy for a pacing site.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). HF causes diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY OF THE INVENTION

The present invention is directed to systems and method for estimating a patient's acute response of a patient to cardiac resynchronization therapy. Methods of the present invention involve measuring systolic timing intervals based on cardiac events for a patient's heart, and classifying a response to pacing as an acute responder or non-responder. A pattern recognition or fusion algorithm may be used to classify the response to pacing.

A confidence indication of the classification may be produced. Classification of an individual patient's response to CRT pacing is preferably based on a patient population for acute CRT responsiveness. A positive indication of an acute response indicates that the pacing site meets cardiac electrical performance criteria and provides for improved patient hemodynamics.

Methods of the present invention involve measuring systolic timing intervals based on cardiac events for a patient's heart. An estimate of a patient's acute response to CRT for a pacing site is determined using the measured systolic timing intervals. The estimate is compared to a threshold. The threshold preferably distinguishes between acute responsiveness and non-responsiveness to CRT for a patient population. An indication of a patient's acute response to CRT for the pacing site may be produced in response to the comparison. The systolic timing intervals may be measured for paced beats associated with the pacing site. The systolic timing intervals may be measured for unpaced beats associated with the pacing site.

Producing the indication of a patient's acute response to CRT may involve producing a binary indication of acute responsiveness to CRT for the pacing site. Producing the indication of a patient's acute response to CRT may involve producing a confidence indication indicative of relative acute responsiveness to CRT for the pacing site. A human perceivable indication of one or both of the binary indication of an acute response to CRT and the confidence indication may be generated. According to one approach, an electrode of an implantable cardiac lead may be implanted at the pacing site in response to a positive indication of an acute response to CRT for the pacing site. One or more pacing parameters, such as an atrio-ventricular delay, may be set for implementing CRT based on a positive indication of an acute response to CRT and the confidence indication.

According to various embodiments, systolic timing intervals are measured in response to pacing the pacing site using one or more atrio-ventricular delay (AVD) values. For example, a short burst pacing protocol may be implemented for a multiplicity of AVD values. The systolic timing intervals may be associated with one or both of mechanical and electrical activity of the patient's heart. For example, the systolic timing intervals may involve measuring timing intervals associated with one or both of heart sounds and arterial blood pressure. Measuring the systolic timing intervals may involve measuring timing intervals associated with cardiac stroke impedance.

In accordance with further embodiments, a medical system of the present invention may include one or more electrodes for delivering pacing pulses to a patient's heart, and an energy delivery and sensing unit coupled to the electrodes. The system may further include a hemodynamic sensor and a memory configured to store at least a threshold that distinguishes between acute responsiveness and non-responsiveness to CRT for a patient population. A controller is coupled to the memory, hemodynamic sensor, and the energy delivery and sensing unit. The controller is configured to measure systolic timing intervals derived from signals produced by the hemodynamic sensor in response to cardiac events, such as pacing pulses delivered to a pacing site of a patient's heart, and to compute an estimate of acute responsiveness to CRT for the pacing site using the measured systolic timing intervals and the threshold.

The controller may be configured to implement a fusion algorithm for computing the estimate of acute responsiveness to CRT for the pacing site. The controller may be configured to compare the estimate to the threshold and produce an indication of acute responsiveness to CRT for the pacing site in response to the comparison.

The hemodynamic sensor may include a sensor configured to sense mechanical activity of the patient's heart. For example, the hemodynamic sensor may include a heart sounds sensor. The hemodynamic sensor may include a sensor configured to sense an electrical parameter associated with the patient's heart. For example, the hemodynamic sensor may include an impedance sensor, such as a cardiac stroke impedance sensor.

The hemodynamic sensor may include a sensor configured to sense mechanical activity of the patient's heart and a sensor configured to sense electrical activity of the patient's heart (e.g., electrocardiograms (ECG) or electrograms (ECG)), and the controller may be configured to measure systolic timing intervals derived from features of signals produced by the mechanical and electrical activity sensors. For example, the hemodynamic sensor may include a cardiac stroke impedance sensor and a heart sounds sensor, and the controller may be configured to measure the systolic timing intervals derived from features of signals produced by the cardiac stroke impedance sensor and the heart sounds sensor. By way of further example, the hemodynamic sensor may include a heart sounds sensor and an electrical sensor that may sense intracardiac electrograms, and the controller may be configured to measure the systolic timing intervals derived from features of signals produced by the heart sounds sensor and the EGM sensor. One such feature could be the pre-ejection period (Q-S1 or R-S1), for example.

The medical system may be configured for implantation in a patient. In some embodiments, at least a portion of the system may be configured for implantation in a patient and another portion of the system may be configured for operation external to the patient. For example, at least a sensor configured for sensing an electrical parameter or electrical activity of the patient's heart may be implantable or configured for invasive use. Other portions of the system, such as a processor, energy delivery circuitry, sensing circuitry, and signal processing software, may be provided in devices and/or systems that reside external of the patient. Such patient-external devices and/or systems may be situated near the patient, such as in the case of a programmer or bed-side communicator, or situated remotely of the patient, such as in the case of a networked advanced patient management system (e.g., distributed systems). Some system elements, such as a processor, memory, or certain software, for example, may be configured for both patient-internal and patient-external use or operation. It is understood that one or more elements of a medical system of the present invention may be configured for implantation in a patient, and one or more elements of the medical system may be configured for patient-external operation, and that the examples of various system configurations described herein are for non-limiting illustrative purposes only.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
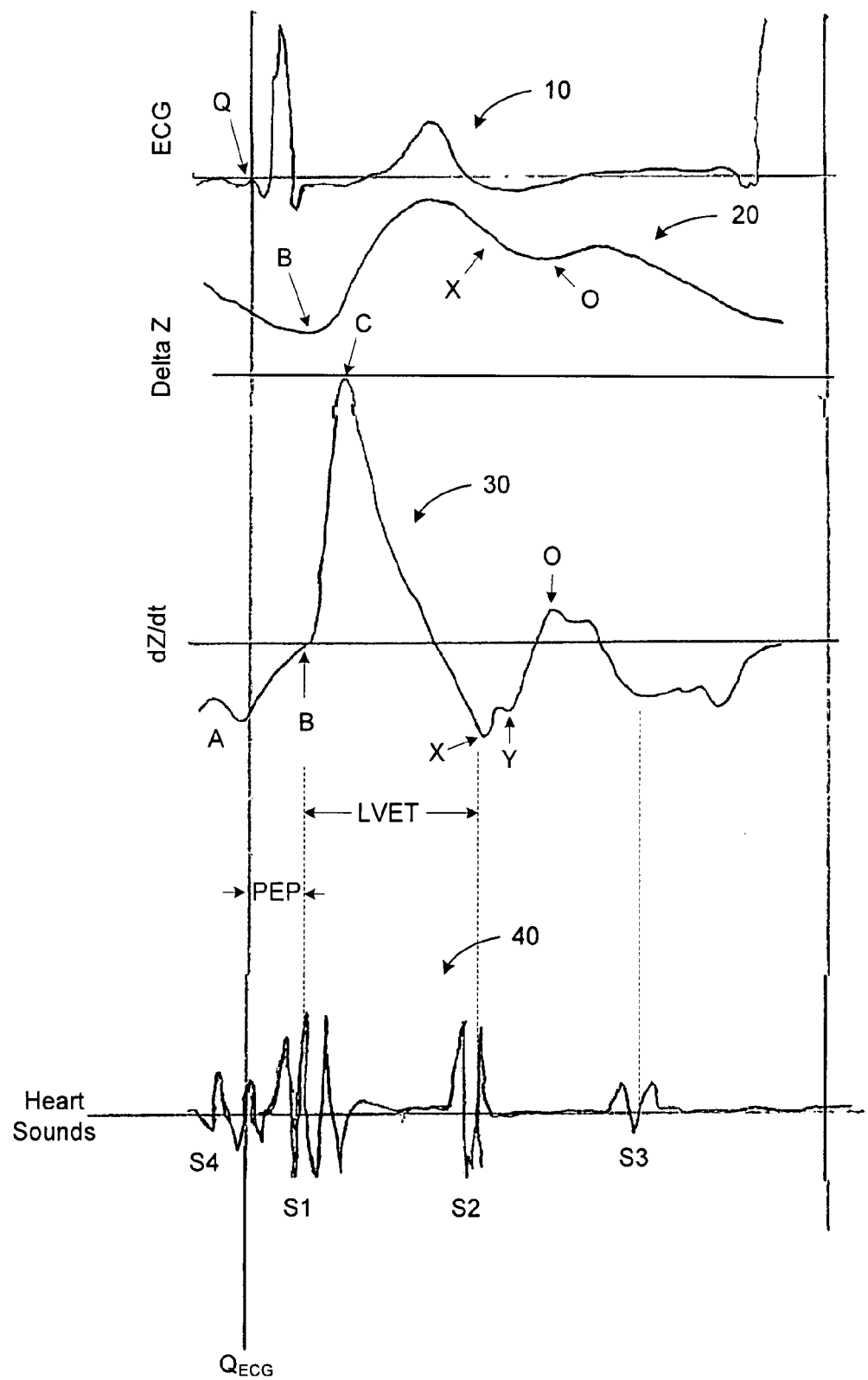
FIG. 1 shows various waveforms depictive of a cardiac cycle, from which timing intervals may be measured and used for evaluating acute responsiveness of a pacing site in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Embodiments of the invention are directed to systems and methods for estimating a patient's acute response to cardiac resynchronization therapy (CRT). Embodiments of the invention are directed to selecting a pacing site for CRT during implant or after implant that provides for improved hemodynamics.

Aspects of the invention involve measuring systolic timing intervals and using a classification methodology to classify a cardiac response to pacing as an acute responder or non-responder to CRT. An acute responder generally refers to a stimulation site and device parameter (e.g., atrio-ventricular delay) that will likely provide a positive hemodynamic response to CRT. A non-responder generally refers to a stimulation site that is unlikely to provide a positive hemodynamic response to CRT. According to embodiments of the invention, a pattern recognition or fusion analysis may be performed to facilitate classification of a cardiac response to pacing as indicative of acute responsiveness or non-responsiveness to CRT. Classification may further involve providing a confidence indication of acute responsiveness or non-responsiveness.

Systems and methods of the invention may involve, for example, measuring systolic timing intervals in response to delivering pacing energy to a pacing site of a patient's heart using one or more pacing parameter values. An estimate of acute responsiveness to cardiac resynchronization therapy (CRT) for the pacing site may be estimated using the measured systolic timing intervals. The estimate may be compared to a threshold. The threshold is preferably developed from data acquired for a population of CRT patients and distinguishes between acute responsiveness and non-responsiveness to CRT. An indication of acute responsiveness to CRT for the pacing site is produced in response to the comparison, such as a signal or a human perceivable indication.

In various embodiments, a binary indication of acute responsiveness to CRT for the pacing site is produced. The binary indication, such as pass/fail or yes/no, provides an immediately understandable indication to an electronic or human recipient that the pacing site is or is not an acute responder site. In addition to the binary indication, a confidence indication indicative of relative acute responsiveness to CRT for the pacing site may also be produced. The confidence indication may be provided in various forms, such as a percentage or probability of certainty, or a gradation or level of confidence, such as high, medium or low.

Methods and systems of the invention provide for identification of candidate pacing sites, such as during an implant procedure, and verification of existing pacing sites, such as during ambulatory evaluation, that a given site is an acute responder site for both electrical and hemodynamic perspectives. A pacing site evaluation methodology of the present invention advantageously provides an indication that a pacing site identified as an acute responder site will likely provide for improved patient hemodynamics relative to pacing sites that merely meet electrical performance requirements for pacing at the site.

Moreover, a determination that a given pacing site will likely provide for improved patient hemodynamics may be made without testing at a multiplicity of sites, comparing results for each of the sites, and selecting the "best" site among those tested based on the comparison. In such conventional approaches, selection of the "best site" is based on electrical performance, typically without quantitatively assessing hemodynamic performance associated with pacing at the "best" site. In contrast to conventional evaluation approaches, a pacing site evaluation methodology of the present invention provides an indication of whether or not a given pacing site is an acute responder that will likely provide for improved patient hemodynamics based on the evaluation performed for the given pacing site, and does not require comparison of testing results for a multiplicity of sites.

Further, it has been found from clinical testing that optimization of pacing parameters, such as atrio-ventricular delay (AVD), is largely solved by determining acute responsiveness of a given pacing site in a manner consistent with methodologies of the present invention. For example, once a pacing site has been identified as an acute responder using methodologies of the present invention, one or more pacing parameters (AVD and/or inter-ventricular delay (IVD)) may be set based on the level of acute responsiveness of the pacing site. For a strong responder site, for example, setting the AVD to about 120 ms is believed adequate. For a weak responder site, longer AVD settings are believed appropriate. For example, weak responder sites or non-responder sites may have associated AVD settings of about 80% of the PR interval, while strong responder sites may have associated AVD settings of about 120 ms.

Turning now to FIG. 1, there is shown various waveforms depictive of a cardiac cycle. FIG. 1 shows waveforms developed from ECG, cardiac stroke impedance, and heart sound sensing. A number of features are also shown for each of the waveforms. Timing intervals useful for evaluating acute responsiveness of a pacing site in accordance with the present invention may be developed based on features of one or a combination of the waveforms shown in FIG. 1. It is understood that timing intervals useful for implementing embodiments of the present invention may be developed using a wide variety of sensors, waveforms, waveform features, and combinations of sensors, waveforms and waveform features, and that those associated with FIG. 1 and other figures are provided for non-limiting illustrative purposes only, and should not be construed as limiting the scope of the present invention.

The waveforms shown in FIG. 1 are generally depictive of a single cardiac cycle, as best seen in the ECG waveform 10. The waveforms 20, 30, 40 are aligned with respect to the initiation of ventricular depolarization as indicated by the Q feature of ECG waveform 10. Waveform 20 represents changes in cardiac stroke impedance during the cardiac cycle. Waveform 30 represents the first derivative of the cardiac stroke impedance waveform 20. Waveform 40 represents heart sounds (S1-S4) associated with different portions of the cardiac cycle.

With reference to waveform 30, and as reflected in waveform 20, various waveform features of interest are identified by letters A, B, C, X, Y, and O. Feature A is associated with contraction of the atria. Feature B is associated with opening of the aortic valve. Feature C is associated with maximum systolic blood flow. Feature X is associated with closure of the aortic valve. Feature Y is associated with closure of the pulmonary valve, and feature O is associated with opening of the mitral valve.

Decreasing rates of cardiac stroke impedance change are recorded as upward deflections in the tracing of waveform 30. The A wave corresponds to atrial systole. The C wave corresponds to the ventricular systole and reflects the rate of change of speed of ejection of the pattern of ejection of blood from the ventricles. The O wave corresponds to ventricular diastole and reflects the rate of change of volume of the atria and veins. Most of the O wave peak corresponds to the mitral opening. The B point and the X point appear immediately after the aortic valve opens and closes, respectively. The B point also coincides with the middle portion of the first heart sound, S1 of waveform 40, and the X point coincides with the second heart sound, S2. The peak C coincides with the peak flow time measured on the ascending aorta. The S3 heart sound occurs after the O wave maximum (during the descending portion) and corresponds to the rapid filling wave of the ventricle. The fourth heart sound, S4, occurs during the second phase of ventricular filling, when the atria contract just prior to S1.

Timing intervals useful in the context of the present invention may be determined using features from any or a combination of the waveforms shown in FIG. 1. For example, a timing interval of interest may be determined from the timing difference between a feature in the impedance signal 20, 30 and a feature in the heart sounds signal 40. The following are non-limiting examples of timing differences of features that may be used in the context of the present invention: S4-B, S4-C, B-S2, C-S2, S1-B, S1-X, S1-Y, S1-O, S2-Y, S2-X, S2-O, X-S3, Y-S3, O-S3. It is noted that each of these timing differences can be calculated from heart sound only or impedance only. For example, left ventricular ejection time (LVET) can be calculated as the S1-S2 duration or the B-X duration.

It is understood that LVET is correlated to stroke volume, cardiac output, and, in general, the systolic performance of the left ventricle. The pre-ejection period (PEP), for example, can be measured as Q-S1 or Q-B and is inversely correlated to systolic performance and stroke volume, and directly correlated with increasing left atrial pressures. The S2-S3 time difference, also measured as B-S3 or S2-O time, is inversely correlated with the left atrial pressures.

Hence, by using a combination of the above timings, reduced stroke volume or increased filling pressures may be detected. For example LVET/PEP is known to be correlated with stroke volume. Also, the time (Q–S1)/(S2–S3) is correlated with left atrial pressures. Using a combination of the above mentioned timing intervals, decompensation can be detected, such as by trending timing intervals and detecting when a threshold has been crossed.

Figure 2:
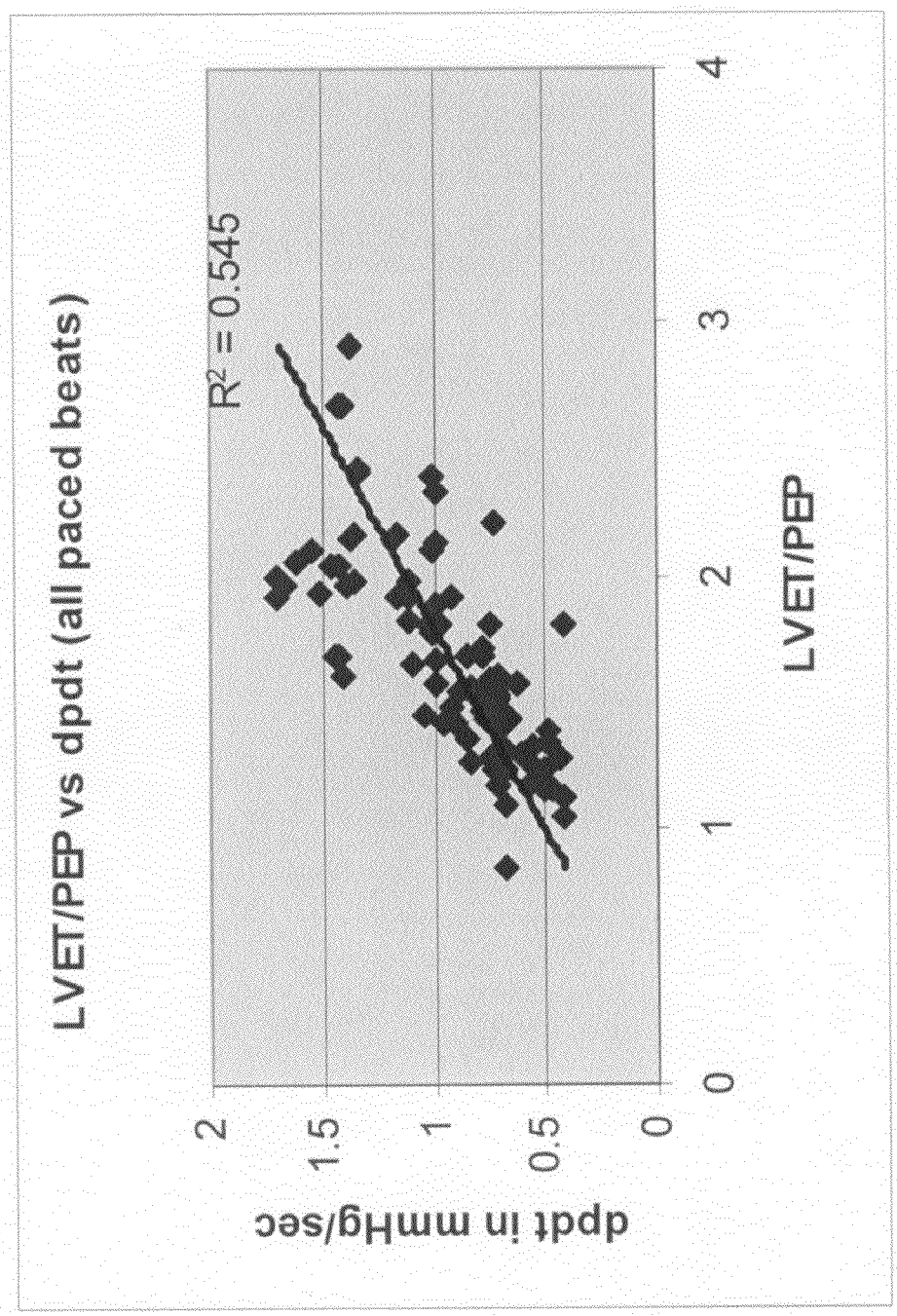
FIG. 2 is a plot of data acquired for a population of CRT patients useful for evaluating a pacing site in accordance with the present invention.

FIG. 2 is a plot of data acquired for a population of CRT patients useful for evaluating a pacing site in accordance with the present invention. The patient population preferably includes patients with implanted cardiac rhythm management devices that provide CRT. Typical patients of interest are those who have implanted CRT devices because of indications such as having QRS complex widths >150 ms or are considered HF class 3 patients. The patient population may also include patients with QRS complex widths of <120 ms, but have other indications that classify them as CRT patients. The data reflected in FIG. 2 was acquired from some 29 patients, from which systolic timing intervals were measured based on left ventricular pressure sensing. As discussed above, equivalent data to that shown in FIG. 2 may be developed from heart sounds data, alone or in combination with pressure data (and/or ECG data).

According to embodiments of the invention, a fusion algorithm may be trained based on acute CRT responsiveness data for a population of CRT patients, such as that shown in FIG. 2. A variety of fusion algorithms and processing methodologies may be used, including, but not limited to, linear regression, Bayesian classification, clustering, support vector machines, neural networks, among others. In general terms, the fusion algorithm and processing methodology is used to combine a multiplicity of systolic timing intervals and to provide an estimate (e.g., probability) that the patient will respond to CRT at the current pacing site. The fusion algorithm may also be implemented to operate on a blending of data types, such as systolic timing intervals and signal amplitudes, feature attributes (e.g., QRS width) or other aspects of sensed physiological or hemodynamic conditions and/or patient demographics. For example, heart sound timing intervals and heart sound amplitudes may be operated on by the fusion algorithm.

In FIG. 2, the ratio of LVET/PEP is shown plotted along the x-axis as a function of peak left ventricular pressure change (y-axis), denoted as dp/dt given in mmHg/sec. The data shown in FIG. 2 was acquired for paced beats, which resulted in stimulation-induced systolic cycles from which systolic timing intervals of interest were measured. The systolic timing interval data acquired for this population of CRT patients was subject to linear regression, which measures the degree of fit between the line and the data points. The square deviations are added to create a measure, $R^2$, referred to as the coefficient of determination or $R^2$ statistic. This statistic measures the goodness of the fit or the amount of variance explained by the regression model, as is well understood in the art. Other statistics associated from the regression model may be of interest, such as the F statistic, which is a measure of confidence of the result.

A logistic regression algorithm, for example, may be developed for a multiplicity of systolic timing intervals and trained based on acute CRT responsiveness data for a population of CRT patients, an example of which is provided below:

$$u = A + B_1 X_1 + B_2 X_2 + \ldots + B_K X_K \quad [1]$$

In Equation [1], the variable $X_1=1/\text{PEP}$, $X_2=\text{LVET}$, and $X_3=1/\text{LVEMD}$, and A is a constant. Each of these variables is shown in FIG. 2, and may be measured from waveform features associated with one or a combination of mechanical (e.g., heart sounds, pressure) features, electrical cardiac activity features, and patient demographic data (e.g., QRS width).

Using the result of Equation [1] above, an estimate of acute responsiveness to CRT therapy for the patient may be determined, such as by using the following equation:

$$\hat{P}_i = \frac{e^u}{1 + e^u} \quad [2]$$

where P-hat is the estimated probability that the $i_{th}$ case is in a category and u is the regular linear regression equation. It is understood that fewer or greater than three variables may be used in the fusion algorithm. For example, additional timing intervals or other physiological or patient-related parameters may be added to Equation [1] above as respective variables $X_4, X_5 \ldots X_K$. The coefficients $B_1 \ldots B_K$ in Equation [1] can be determined from the training of the linear regression algorithm using patient population data. The accuracy of the estimate produced by Equations [1] and [2] above can be improved by increasing the amount and quality of patient population data used to train the fusion algorithm.

The estimate or probability provided by the fusion algorithm is preferably compared to a threshold that distinguishes between acute responsiveness and non-responsiveness to CRT for a patient population, as indicated in the following equation:

If $P(\text{response}) \geq Th$, then patient is an acute responder

If $P(\text{response}) < Th$, then patient is a non-responder [3]

where P(response) refers to the estimate or probability of responsiveness indicated by the fusion algorithm result, and Th is the threshold that distinguishes between acute responsiveness and non-responsiveness to CRT for a patient population.

The threshold is preferably associated with a sensitivity and specificity that can reliably distinguish between acute responsiveness and non-responsiveness to CRT for a patient population. Sensitivity refers to the ability of a test to detect a condition when present. Specificity refers to the ability of a test to exclude a condition when it is absent. The higher the specificity, the lower the false positives. For example, the threshold may be associated with a sensitivity of 90% and a specificity of 80%.

Figure 3:
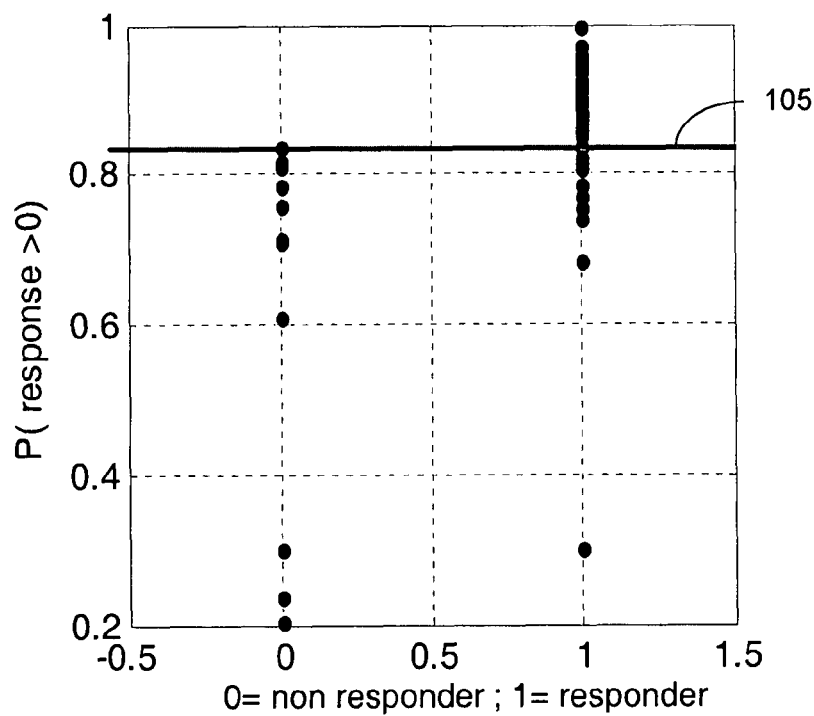
FIGS. 3 and 5 are plots that illustrate a threshold that is selected to distinguish between acute responders and non-responders for a population of CRT patients in accordance with embodiments of the present invention.
Figure 4:
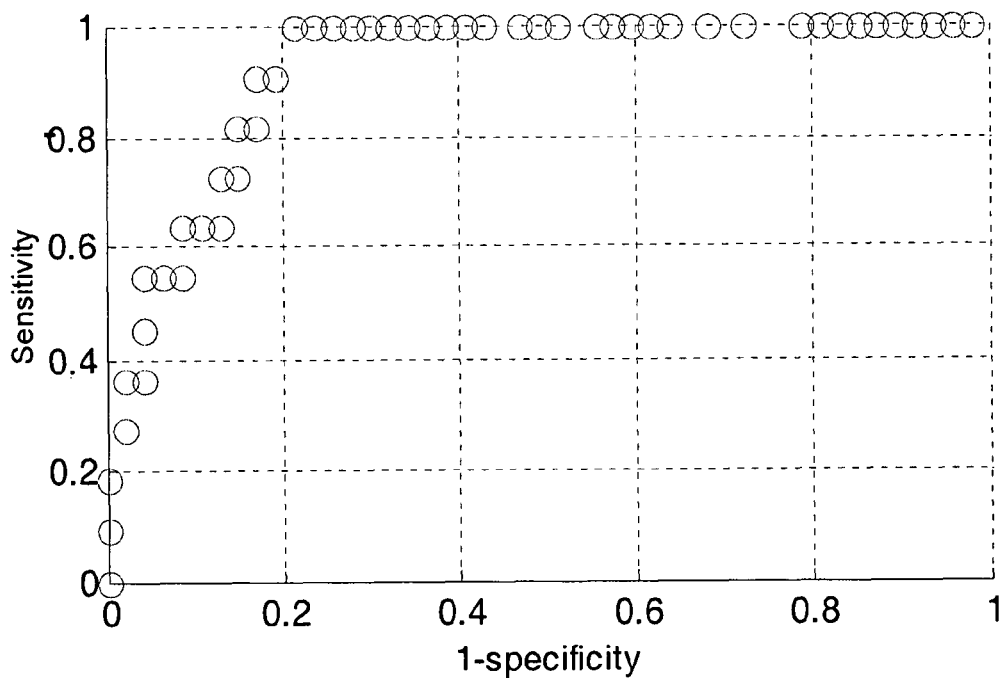
FIGS. 4 and 6 are plots of specificity (1-specificity) versus sensitivity for acute responsiveness detection, which may be determined using the threshold shown in FIGS. 4 and 6, respectively.
Figure 5:
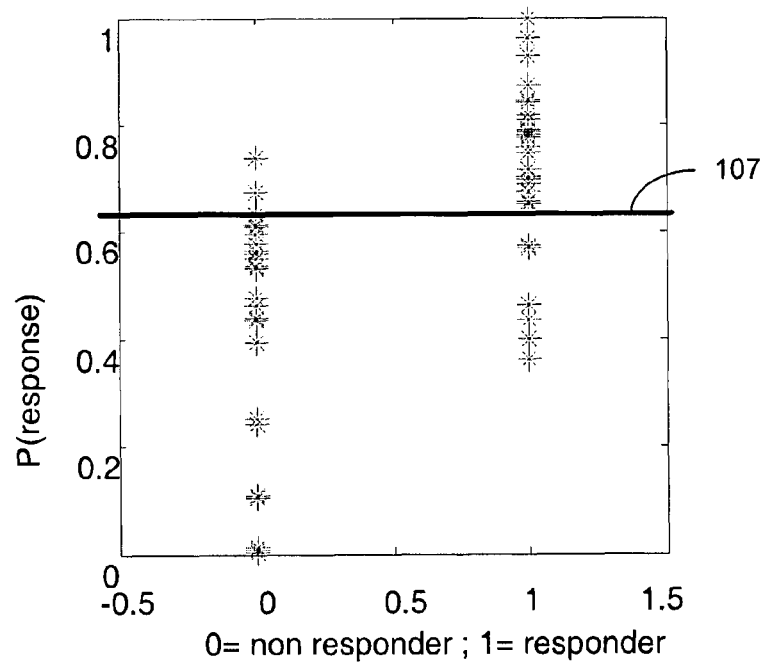
Figure 6:
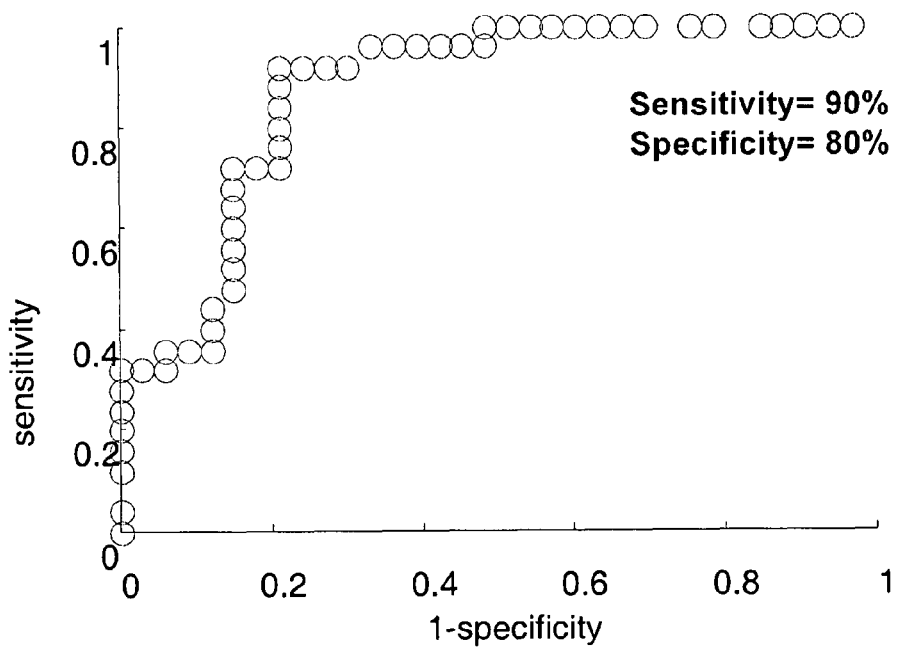

Turning now to FIGS. 3-6, these figures illustrate examples of thresholds developed in accordance with the present invention and the relationship between thresholds and associated sensitivity and specificity values. FIGS. 3 and 4 correspond to a response defined as the change in LVdpdt>0% from baseline. That is, if a patient has a dpdt of 1000 at baseline and if pacing changes the dpdt to 999, for example, then the patient is a non-responder. If, however, pacing changes the dpdt to 1001, then the patient is a responder. FIGS. 5 and 6 correspond to a response defined as the change in LVdpdt>5% from baseline. That is, if a patient has a dpdt of 1000 at baseline and if pacing changes the dpdt to 1010, for example, then the patient is a non-responder, since the change is only 1% compared to the baseline of 1000. If, however, pacing changes the dpdt to 1051, then the patient is a responder, since an acute response in this illustrative example is defined as a change of at least 5% of LVdpdt from baseline.

The baseline may be established in several ways. According to one approach, the baseline may be determined from systolic timing intervals measured for sensed beats. In embodiments where additional sensor measurements and/or demographic data is used, this data is also acquired for sensed beats. According to another approach, the baseline may be obtained via right ventricular-only pacing (i.e., without left ventricular pacing). Other approaches for establishing the baseline from which responsiveness to pacing can be determined are also contemplated.

In accordance with one approach for establishing the baseline, a lead may be placed at appropriate locations in or on the heart. Systolic timing intervals may be measured for a number of unpaced beats (i.e., sensed beats). Additional systolic timing intervals may be measured for paced beats, preferably using several different atrio-ventricular delay settings. The systolic timing intervals measured for both paced and sensed beats may then be used to assess the patient's response.

The plot of FIG. 3 illustrates a threshold 105 that is selected to distinguish between acute responders and non-responders for a population of CRT patients. The value of 0 along the x-axis indicates non-responders and the value of 1 indicates responders to CRT. As is shown in FIG. 3, the threshold 105 is selected so that the acute responders are distinguished from non-responders with relatively no overlap between these two classes. In this regard, the threshold 105 is associated with a relatively high sensitivity and a relatively high specificity, as indicated in FIG. 4. In the illustrative example of FIG. 3, the threshold is about 0.82.

In FIG. 5, the threshold 107 is selected to that the acute responders are distinguished from non-responders with some degree of overlap between these two classes. In this regard, the threshold 107 is associated with a relatively high sensitivity and a moderately high specificity, as indicated in FIG. 6. In the illustrative example of FIG. 5, the threshold is about 0.64. It has been found that reliable determinations of acute responsiveness to CRT for a patient can be achieved using a threshold that is associated with a relatively high sensitivity and a moderately high specificity, such as that shown in FIG. 5.

Figure 7:
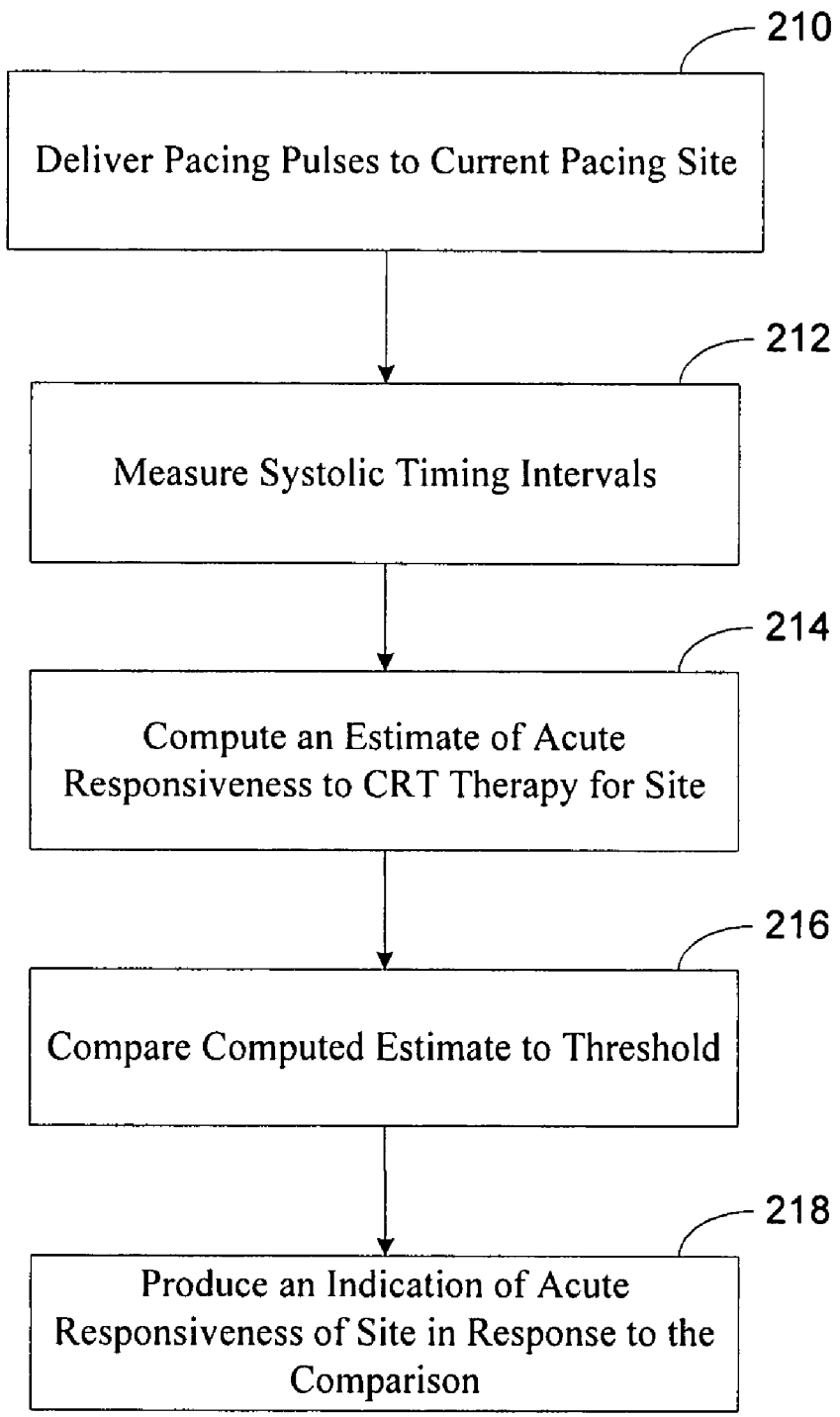
FIGS. 7 and 8 are flow charts that illustrate various processes associated with a pacing site evaluation methodology in accordance with embodiments of the present invention.

Turning now to FIG. 7, there is shown a flow chart that illustrates various processes associated with a pacing site evaluation methodology of the present invention. The evaluation involves delivering pacing pulses to a current pacing site 210. The pacing site may be a site at which a pacing electrode is presently implanted or a candidate site for implantation. A short burst pacing protocol is preferably implemented by the implanted cardiac rhythm management (CRM) device, so that baroreflex is not activated, and afterload is held steady. The pacing protocol may be implemented using one or more predetermined pacing parameter values (e.g., AVD and/or IVD) or a range of pacing parameter values. For example, the pacing protocol may be implemented by sweeping through a multiplicity of AVD value settings.

The pacing protocol produces stimulation-induced systolic cycles from which various systolic timing intervals may be measured 212. As discussed previously, a wide variety of timing intervals and timing interval combinations may developed from sensing of electrical and/or mechanical activity of the heart. It is noted that the sensor or sensors used to sense electrical and/or mechanical activity of the heart may be implanted, patient-external or a combination thereof. For example, an electrical and/or mechanical heart activity sensor (e.g., heart sound sensor, such as a microphone or accelerometer) may be positioned on the outer skin surface of the patient during a pacing electrode implant procedure. In an ambulatory scenario, an implanted electrical and/or mechanical heart activity sensor may be used to sense cardiac activity from which timing intervals of interest may be measured. The systolic timing intervals may include those identified hereinabove, such as LVET and PEP in particular.

An estimate of acute responsiveness to CRT is computed 214 for the site, preferably by using the methodology discussed above. The computed estimate may then be compared 216 to a threshold, such as that discussed above. An indication of acute responsiveness of the site may be produced 218 based on the comparison. The indication may involve generation of a signal that can be communicated to a processor or other device, such as a programmer, portable communicator, or network interface of an advanced patient management system, for example. A human perceivable indication of acute responsiveness may be produced, such as a message presented on a display or activation of a visual/audible indicator (e.g., audible tone, LED illumination or flashing) that indicates the result of the comparison operation.

In various embodiments, a binary indication of acute responsiveness to CRT for the pacing site is produced to indicate the result of the comparison operation. The binary indication may be a pass/fail or yes/no indication of whether or not the pacing site is an acute responder site. A confidence indication representative of relative acute responsiveness to CRT for the pacing site may also be produced. As previously discussed, the confidence indication may be provided in various forms, such as a percentage or probability of certainty, variance, or a gradation or level of confidence, such as high, medium or low.

Figure 8:
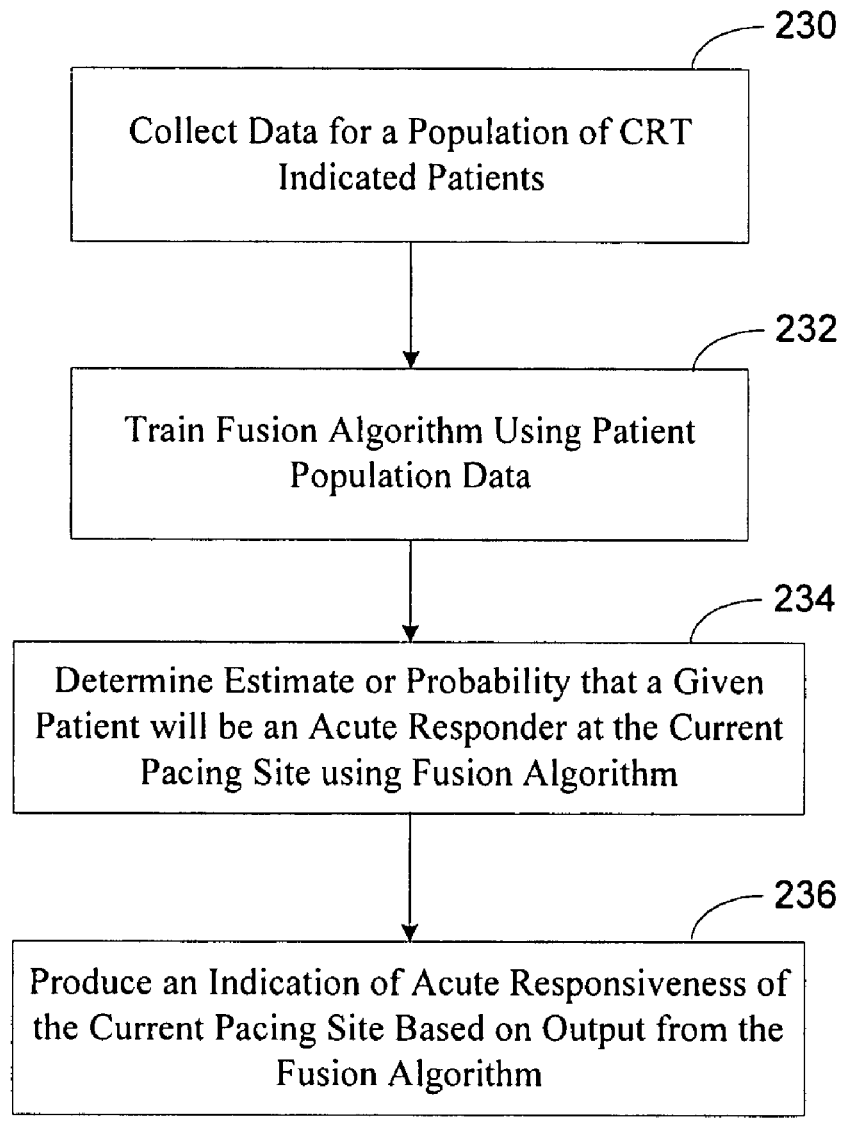

FIG. 8 illustrates various processes associated with a pacing site evaluation methodology of the present invention. In particular, FIG. 8 illustrates a methodology involving collection 230 of data for a population of CRT indicated patients. A fusion algorithm may be trained 232 using the patient population data. Useful fusion algorithms that may be employed include any regression or classification algorithm can be used to predict CRT responsiveness at a pacing site. Such fusion algorithms include linear regression, a linear discriminate analysis-based classifier, support vector machines for both regression and classification, and neural networks, among others. Based on fusion algorithm training, a threshold that distinguishes between acute responder sites and non-responder sites may be set.

Using the fusion algorithm, an estimate or probability that a given pacing site will be an acute responder site for a particular patient may be determined 234, which generally involves comparing the estimate or probability to a pre-established threshold of the type discussed above. An indication of acute responsiveness or non-responsiveness of the current pacing site may be produced 236 based on the output from the fusion algorithm.

A pacing site evaluation methodology of the present invention may be implemented in a variety of medical diagnostic devices and systems, include implantable and patient-external devices and systems. For example, a pacing site evaluation methodology of the present invention may be implemented entirely by an implanted device (e.g., pacemaker, ICD, CRT devices), entirely by a patient-external system (other than cardiac electrodes/leads) or in a distributed manner by both implanted and patient-external devices or systems. In the context of a patient-external or distributed approach, various external systems may be employed, such as a programmer and/or a networked system, such as an advanced patient management system.

Figure 9:
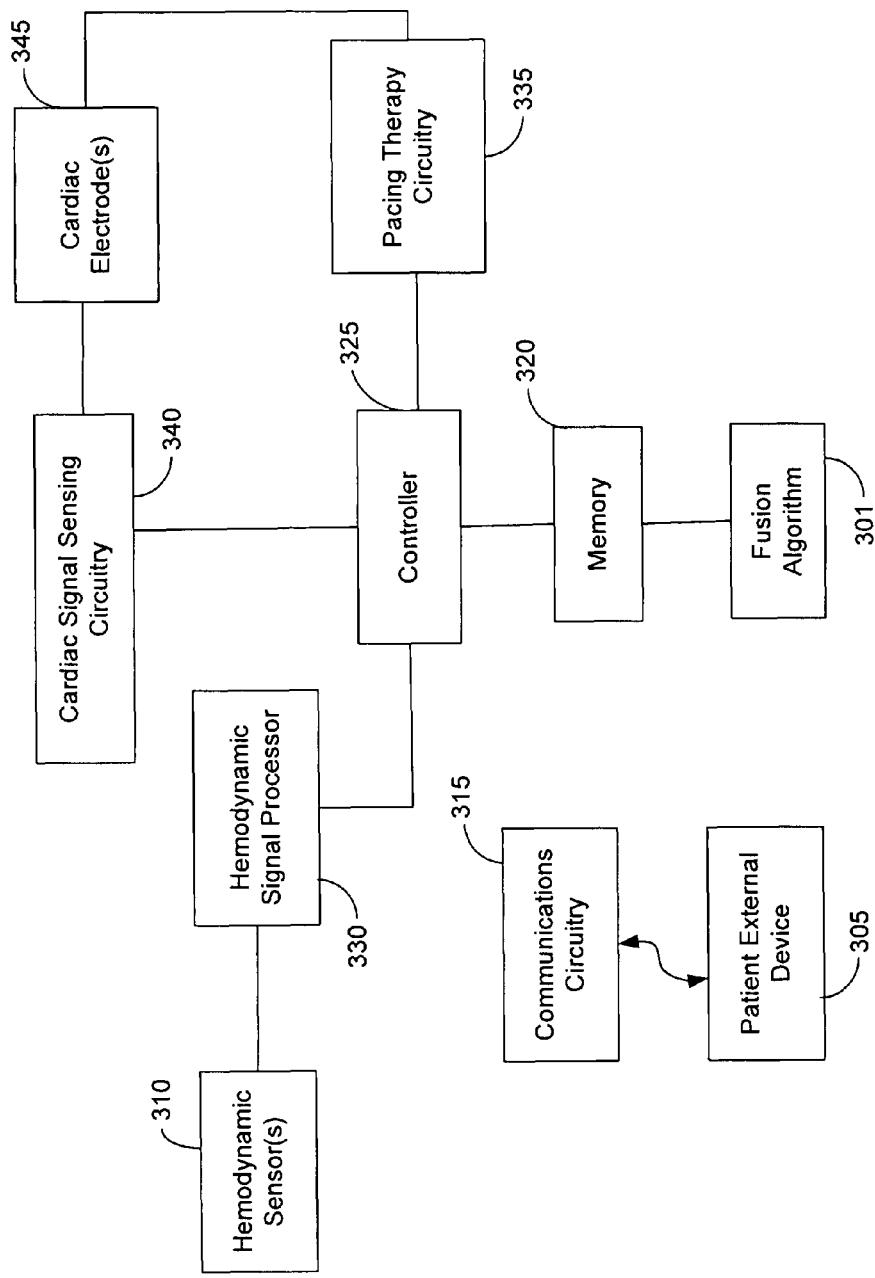
FIG. 9 is a block diagram of circuitry that may be used for implementing a pacing site evaluation methodology in accordance with embodiments of the present invention.

FIG. 9 is a block diagram of circuitry that implements a pacing site evaluation methodology in accordance with embodiments of the invention. One or more cardiac electrodes 345 may be positioned or disposed at multiple locations within a heart chamber or vasculature. In the context of an electrode implantation procedure, a candidate pacing site may be evaluated using a lead that includes one or more electrodes. In the context of post-implant evaluations, one or more implanted pacing sites may be evaluated.

One or more sensors 310 are configured to sense physiological factors indicative of a patient's hemodynamic status. Useful sensors 310 include a sensor or sensors that detect heart sounds (e.g., microphone, accelerometer), a pressure sensor (e.g., left arterial pressure sensor such as a pulmonary artery pressure sensor, right ventricular pressure sensor), and a cardiac stroke impedance sensor, among others. Signals produced by the one or more sensors 310 may be communicated to a hemodynamic signal processor 330, which processes the sensor signals for use by a controller 325.

The controller 325 is coupled to the hemodynamic signal processor 330, memory 320, cardiac signal sensing circuitry 340, and pacing therapy circuitry 335. The memory 320 is configured to store program instructions and/or data. In addition, the stored information may be used to provide a log of events for display or analysis at a later time. The memory 320 may be configured to store a fusion algorithm 301 and a threshold of a type described previously. Alternatively, the fusion algorithm 301 may be stored on a patient-external device or system. The controller 325 executes program instructions to implement a pacing site evaluation procedure in accordance with embodiments of the present invention.

The controller 325 is preferably coupled to communications circuitry 315 which allows the device to communicate with other devices, such as a patient-external programmer or advanced patient management system. In some implementations, an advanced patient management (APM) system may be used to collect CRT patient data for purposes of developing patient population data from which a fusion algorithm may be trained. This data may be acquired from numerous CRT patients. The APM system or programmer may also be used to implement or facilitate implementation of the pacing site evaluation methodology of the present invention, particularly in the context of an electrode implantation procedure. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 10:
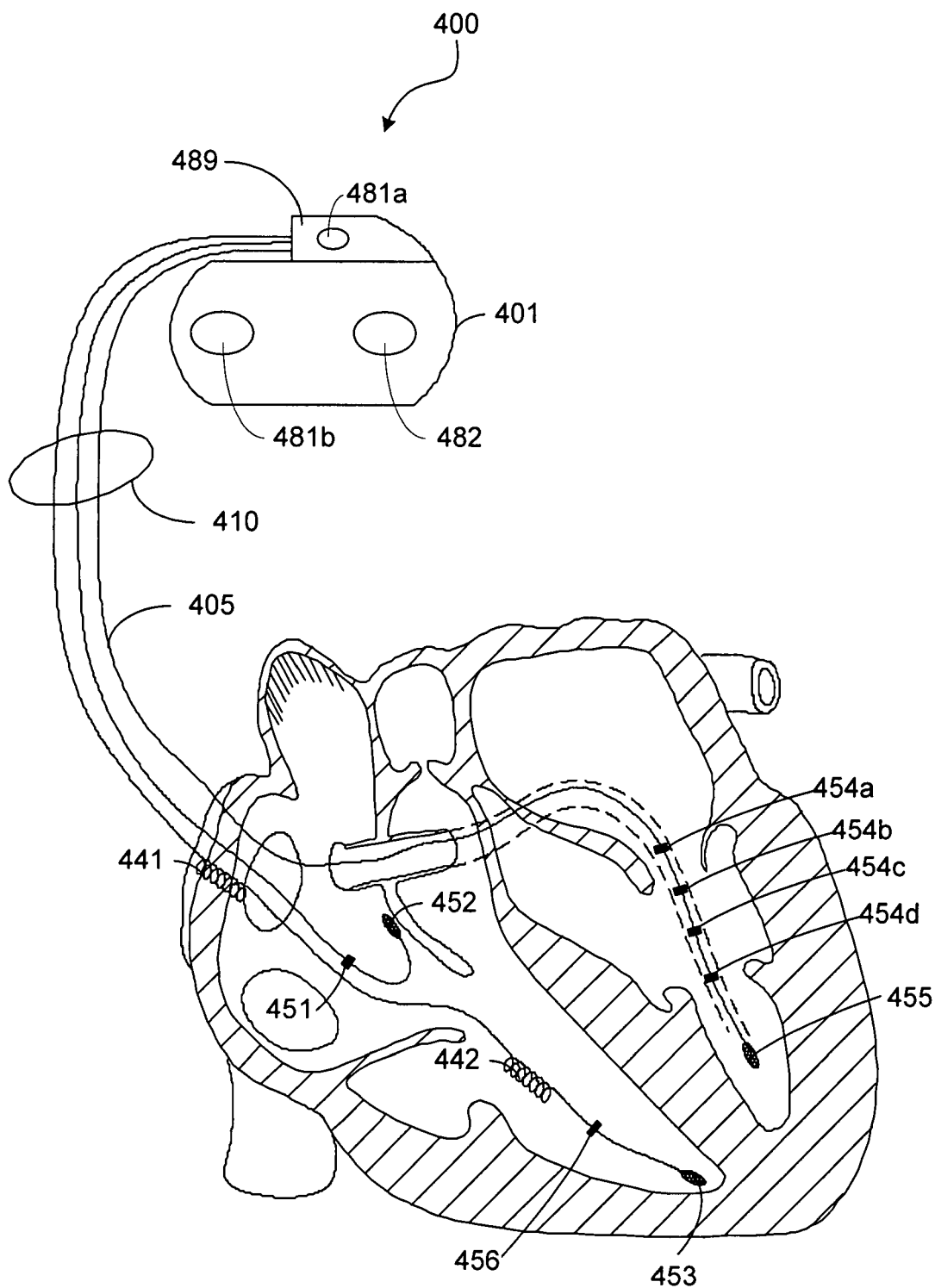
FIG. 10 illustrates a patient-implantable device that may be used in conjunction with a pacing site evaluation methodology in accordance with embodiments of the present invention.

FIG. 10 shows an embodiment of the present invention implemented with use of an implanted cardiac therapy device 400. The therapy device 400 includes cardiac rhythm management circuitry enclosed within an implantable housing 401. The CRM circuitry is electrically coupled to an intracardiac lead system 410. Portions of the intracardiac lead system 410 are shown inserted into the patient's heart. The lead system 410 includes cardiac pace/sense electrodes 451-456 positioned in, on, or about one or more heart chambers for sensing electrical signals from the patient's heart and/or delivering pacing pulses to the heart. The intracardiac sense/pace electrodes 451-456 may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The left ventricular lead 405 incorporates multiple electrodes 454a-454d positioned at various locations within, on or about the left ventricle. Stimulating the ventricle at multiple locations or at a single selected location may provide for increased cardiac output in a patients suffering from HF. In accordance with various embodiments described herein, one or more of the electrodes 454a-454d are selected for pacing the left ventricle. In other embodiments, leads having multiple pacing electrodes positioned at multiple locations within a chamber, such as the one illustrated by the left ventricular lead 405 of FIG. 10, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 401 of the implantable device 400 may optionally serve as one or multiple can or indifferent electrodes. The housing 401 is illustrated as incorporating a header 489 that may be configured to facilitate removable attachment between one or more leads and the housing 401. The housing 401 of the therapy device 400 may include one or more can electrodes 481b. The header 489 of the therapy device 400 may include one or more indifferent electrodes 481a.

The housing 401 and/or header 489 may include one or more hemodynamic sensors 482, such as an accelerometer or microphone. One or more cardiac leads 410 or separate sensor leads may incorporate one or more hemodynamic sensors, such as a pulmonary arterial pressure sensor. The cardiac electrodes and/or other sensors disposed within or on the housing 401 or lead system 410 of the therapy device 400 may produce signals used for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters. It is contemplated that, in certain embodiments, information derived from such signals may be incorporated into the fusion algorithm that is employed to determine acute responsiveness of a pacing site to CRT.

In some configurations, the implantable device 400 may incorporate one or more transthoracic impedance sensors that may be used to acquire the patient's respiratory waveform, and/or to acquire other respiratory-related information. The transthoracic impedance sensor may include, for example, one or more intracardiac electrodes 441, 442, 451-456 positioned in one or more chambers of the heart. The intracardiac electrodes 441, 442, 451-456 may be coupled to impedance drive/sense circuitry positioned within the housing 401 of the therapy device 400. Information from the transthoracic impedance sensor may be used to adapt the rate of pacing to correspond to the patient's activity or metabolic need, among other uses.

Communications circuitry is disposed within the housing 401 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 400 may include circuitry for detecting and treating cardiac tachyarrhythmia via defibrillation therapy and/or anti-tachyarrhythmia pacing (ATP). Configurations providing defibrillation capability may make use of defibrillation coils 441, 442 for delivering high energy shocks to the heart to terminate or mitigate tachyarrhythmia.

In some embodiments, the implantable therapy device 400 may include circuitry for selection of pacing electrode(s), timing sequence, and/or amplitude or pulse waveform output configurations (collectively referred to as pacing output configuration) to be applied via one or multiple electrodes within one or multiple heart chambers. For example, a pacing site evaluation procedure may be implemented to evaluate, after implant, whether a particular pacing site continues to qualify as an acute responder site. In the event of an adverse change in CRT responsiveness occurring at a particular pacing site, alternative pacing sites or vectors may be evaluated in accordance with the pacing site evaluation methodologies of the present invention. A change may be made in the pacing output configuration in response to the evaluation. For example, in a pacemaker equipped with multiple pacing electrodes respectively disposed at multiple pacing sites within a heart chamber, the ability to select one or more electrodes, temporal sequence, and/or pulse waveform characteristics for delivery of pacing can be used enhance the contractile function of the heart chamber.

Multi-site pacemakers, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, anodal/cathodal polarity and/or waveshape of the pacing pulses may also be altered to enhance pumping function.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical system, comprising:
   an electrode for delivering at least one pacing pulse to a pacing site of a patient's heart during a cardiac cycle;
   an energy delivery and sensing unit coupled to the electrode;
   a hemodynamic sensor;
   another sensor;
   a memory configured to store at least a threshold that distinguishes between acute responsiveness and non-responsiveness to cardiac resynchronization therapy (CRT) for a patient population, patient population data, and a fusion algorithm; and
   a controller coupled to the memory, the hemodynamic sensor, the another sensor, and the energy delivery and sensing unit, the controller configured to:
   measure systolic timing intervals of a plurality of different events of the cardiac cycle derived from a plurality of signals sensed during the cardiac cycle, at least one of the plurality of signals produced by the hemodynamic sensor and indicating a systolic timing interval of a mechanical cardiac event of the plurality of different events of the cardiac cycle, and at least another of the plurality of signals produced by the another sensor,
   implement the fusion algorithm to combine the measured systolic timing intervals of the plurality of different events of the cardiac cycle and the patient population data to compute an estimate of probability of acute responsiveness to cardiac resynchronization therapy CRT for the pacing site,
   compare the estimate to the threshold, and
   generate an output indication of acute responsiveness or non-responsiveness of the pacing site to CRT based on the comparison of the estimate to the threshold.

2. The medical system of claim 1, wherein all of the plurality of systolic timing intervals are intervals of different mechanical events of the cardiac cycle.

3. The medical system of claim 1, wherein the controller is configured to measure signal amplitude from at least one of the signals of the plurality and implement the fusion algorithm using the measured systolic timing intervals and the at least one measured signal amplitude.

4. The medical system of claim 1, wherein controller implementation of the fusion algorithm comprises use of a linear regression parameter generated from the measured systolic timing intervals in computing the estimate.

5. The medical system of claim 1, wherein at least one of the signals of the plurality from which at least one of the systolic timing intervals is measured comprises an electrical cardiac signal indicating electrical activity of the heart during the cardiac cycle.

6. The medical system of claim 1, wherein the hemodynamic sensor comprises a cardiac stroke impedance sensor.

7. The medical system of claim 1, wherein the hemodynamic sensor comprises a heart sounds sensor.

8. The medical system of claim 1, wherein the hemodynamic sensor comprises a cardiac stroke impedance sensor and a heart sounds sensor, the controller measuring the systolic timing intervals derived from features of signals produced by the cardiac stroke impedance sensor and the heart sounds sensor.

9. The medical system of claim 1, wherein the system is configured for implantation in a patient.

10. The medical system of claim 1, wherein at least a portion of the system is configured for implantation in a patient and another portion of the system is configured for operation external to the patient.

11. The medical system of claim 1, wherein the plurality of systolic timing intervals are intervals of different electromechanical events of the cardiac cycle.

12. The medical system of claim 1, wherein the computed estimate of acute responsiveness is a binary indication between acute responsiveness and non-responsiveness to CRT for the pacing cite.

13. The medical system of claim 1, wherein the controller is further configured to calculate a confidence indication indicative of relative acute responsiveness to CRT for the pacing site.

14. The medical system of claim 13, wherein the controller is further configured to set an atrio-ventricular delay for the CRT based on the estimate of acute responsiveness to CRT and the confidence indication.

15. The medical system of claim 1, further comprising circuitry configured to output a human perceivable indication indicative of the computed estimate of acute responsiveness to CRT.

16. The medical system of claim 1, wherein the systolic timing intervals are measured in response to delivery of the at least one pacing pulse using one or more atrio-ventricular delay values.

17. The medical system of claim 1, wherein the hemodynamic sensor comprises an arteriole blood pressure sensor configured for implantation and to measure pressure of the arteriole system.

18. A medical system for delivering at least one pacing pulse to a pacing site of a patient's heart during a cardiac cycle, the system comprising:
  means for measuring systolic timing intervals of a plurality of different events of the cardiac cycle, at least one of the systolic timing intervals based on a mechanical cardiac event, the measuring means comprising at least a hemodynamic sensor and another sensor;
  means for storing patient population data;
  means for implementing a fusion algorithm to combine the measured systolic timing intervals of the plurality of different events of the cardiac cycle and the patient population data to compute an estimate of acute responsiveness to cardiac resynchronization therapy (CRT);
  means for comparing the estimate to a threshold, the threshold distinguishing between acute responsiveness and non-responsiveness to CRT for a patient population; and
  means for producing an indication of acute responsiveness to CRT for the pacing site in response to the comparison.

* * * * *

UNITED STATES PATENT AND TRADEMARK OFFICE
CERTIFICATE OF CORRECTION

PATENT NO.         : 8,229,557 B2
APPLICATION NO.    : 11/729453
DATED              : July 24, 2012
INVENTOR(S)        : Patangay et al.

It is certified that error appears in the above-identified patent and that said Letters Patent is hereby corrected as shown below:

In the Claims

Column 14, line 45, Claim 1: "to cardiac resynchronization therapy CRT" should read --to CRT--.

Column 15, line 24, Claim 12: "pacing cite" should read --pacing site--.

Signed and Sealed this
Sixth Day of November, 2012

David J. Kappos
*Director of the United States Patent and Trademark Office*